United States Patent [19]

Page et al.

[11] Patent Number: 5,032,513

[45] Date of Patent: Jul. 16, 1991

[54] PROCESS FOR THE PREPARATION OF GAMMA AND DELTA LACTONES

[75] Inventors: Gregory V. Page, Maplewood, N.J.; Robert G. Eilerman, Merrick, N.Y.

[73] Assignee: BASF Corporation, Clifton, N.J.

[21] Appl. No.: 201,087

[22] Filed: Jun. 1, 1988

[51] Int. Cl.$^5$ .................. C12P 17/06; C12P 17/04; C12P 17/00; A23L 1/226

[52] U.S. Cl. .................................. 435/125; 435/126; 435/123; 435/146; 435/931; 426/536

[58] Field of Search ................ 435/125, 126, 146, 931

[56] References Cited

U.S. PATENT DOCUMENTS

| | | |
|---|---|---|
| 3,076,750 | 2/1963 | Muys et al. |
| 4,138,289 | 2/1979 | Barner et al. ................... 435/146 X |
| 4,451,565 | 5/1984 | Gatfield et al. ..................... 435/117 |
| 4,542,097 | 9/1985 | Labows, Jr. |
| 4,560,656 | 12/1985 | Farbood |
| 4,873,194 | 10/1989 | Sawamura et al. ................. 435/198 |

OTHER PUBLICATIONS

Tahara, S. et al., 1978, Agric. Biol. Chem., vol. 42, No. 4, pp. 879–883.
Lehninger, A., 1975, *Biochemistry*, 2nd Edition, Worth Publishers, N.Y., pp. 500–502.
Hoffman, B., and Rehm, H. J., 1976, "Degradation of Long Chain n-Alkanes by Mucorales," European Journal of Applied Microbiology, vol. 3, pp. 31–41.
Collins and Halim, "Characterization of the Major Aroma Constituent of the Fungus Trichoderma Viride (Pers.)", J. Agric. Food Chem., 20: 437–438 (1972).
Drawert et al., "Concerning the Biosynthesis of Aroma Materials by Micro-Organisms", Chem. Mikrobiol. Technol. Lebensm., 8:91–92 (1983).
Anderson and Edwards, "Metabolites of the Higher Fungi, Part 19, Serpenone, 3-Methoxy-4-Methyl-5-Prop-1-Enylfuran-2(5H)-One, A New Gamma Butyrolactone from the Fungus Hypoxylon Serpens (Barrons Strain) (Persoon Ex Fries)Kickx", J. Chem. Soc., Perkin Trans. 1, 215–221 (1982).
Jourdain et al., "Aroma Components Production by Immobilized Microbial Cells", Topics in Flavor Research, pp. 427–441 (1985).
Sarris and Latrasse, "Production of Odiferous Gamma Lactones by Fusarium Poae", Agric. Biol. Chem., 49: 3227–3230 (1983).
Tahara et al., "Gamma-Decalactone-One of Constituents of Volatiles in Cultured Broth of Sporobolomyies Odorus", Agric. Biol. Chem., 36: 2585–2587 (1972).
Vesonder et al., "Formation of the Delta-Lactone of 3,5-Dihydroxydecanoic Acid by the Fungus Cephalosporium Recifei", Can. J. Biochem., 50: 363–365 (1972).
Joseph A. Maga, "Lactones in Foods", Critical Reviews in Food Science and Nutrition, Sep. 1–56 (1976).
Roland Tressel et al., "Formation of Lactones and Terpenoids by Microorganisms", Flavor of Foods and Beverages, 145–168 (1978).
F. M. Yong et al., "Effect of Nitrogen Source on Aroma Production by Trichoderma viride", Appl. Microbiol. Biotechnol., 22:146–147 (1985).
Lanza et al., "Aroma Production by Cultures of Ceratocystis moniliformis", J. Agrtic. Food Chem., vol. 24, No. 4, 1247–1249 (1976).

*Primary Examiner*—Douglas W. Robinson
*Assistant Examiner*—Mary E. Mosher
*Attorney, Agent, or Firm*—Kenyon & Kenyon

[57] ABSTRACT

A process for the preparation of gamma and delta lactones from organic carboxylic acids or derivatives thereof is disclosed. The process comprises cultivating, under aerobic conditions, a fungus of the genus Mucor in a suitable medium containing the carboxylic acid or a derivative thereof.

27 Claims, No Drawings

PROCESS FOR THE PREPARATION OF GAMMA AND DELTA LACTONES

BACKGROUND OF THE INVENTION

Lactones are known to possess useful organoleptic properties and have been employed as flavor and fragrance materials. For example, Maga, in a comprehensive survey published in "Critical Reviews in Food Science and Nutrition", September, 1976, pp 1-56, summarized the aroma and flavor properties of naturally derived lactones. According to Maga, gamma-hexalactone possesses a herbaceous, sweet odor with a coumarin, caramel taste. Gamma-octalactone has a fruity, coconut odor and taste, while gamma- and delta- decalactones exhibit a fruity, peach-like odor and taste.

The herbaceous or fruit origin of many of the foregoing lactones has been well established. However, their isolation from plant material by extraction or distillation is often impractical or impossible because they are present in extremely low concentrations. Consequently, synthetic reaction methods are often used to manufacture lactones for use as flavor and fragrance materials.

Lactones have also been identified among the metabolites of various microorganisms. For example, Collins and Halim (*J. Agric. Food Chem.*, 1972, 20, 437) identified the delta-lactone, 6-pentyl-2-pyrone, as the predominant volatile material arising from a culture containing the soil fungus *Trichoderma viride*. Drawert, et. al. (*Chem. Mikrobiol. Technol. Lebensum.*, 1983, 8, 91) identified milligram quantities of $C_3$-$C_8$ gamma-lactones from cultures of *Polyporus durus* in a nutrient broth. Likewise, similar yields of a series of gamma-lactones from a cultured malt broth of *Fusarium poae* were reported by Sarris and Latrasse (*Agric. Biol. Chem.*, 1983, 49, 3227). U.S. Pat. No. 4,542,097 discloses the use of *Pityrosporum* cultures for the production of mixtures of gamma-lactones in low yields. Tahara, et. al., (*Agric. Biol. Chem.*, 1972, 36, 2585) found that the microorganism *Sporobolomyces odorus* produced milligram quantities of gamma-decalactone in a 15 L fermentation broth after an extended incubation period.

The metabolism of ricinoleic acid by several *Candida* strains was investigated by Okui, et. al., (*J. Biochemistry*, 1963, 54, 536) who showed that gamma-hydroxydecanoic acid was an intermediate in the oxidative degradation pathway. Farbood and Willis in U.S. Pat. No. 4,560,656, studied this beta-oxidation process in greater detail with castor oil. With a variety of microorganisms, they were able to produce gamma-hydroxydecanoic acid and subsequently gammadecalactone at a level of 5 to 6 grams per liter of fermentation broth.

Methods have also been disclosed for the preparation of certain optically active lactones and the corresponding hydroxy carboxylic acids through microbial reduction of ketocarboxylic acids. For example, U.S. Pat. No. 3,076,750 discloses a process for the microbial reduction of 4- and 5-ketocarboxylic acids having from 5 to 18 carbon atoms.

The use of a microbial process to produce lactones, such as those described above, would appear to have advantages over synthetic methods because the microbial process combines into a single step the multiple reactions required by a synthetic method. Moreover, the microbial process would satisfy the desire to obtain flavor and fragrance material from natural sources.

However, like processes utilizing plant extraction, the microbial processes described in the literature suffer from extremely poor yields and are not general in nature. They produce only certain, specific lactones and are not known to be useful for the production of lactones of varying molecular weight.

Accordingly, it is an object of the invention to develop a microbiological process for the production of lactones of variable carbon chain length. It is also desired to produce gamma or delta lactones. Yet another object is the microbiological production of such lactones with yields that will establish economical lactone manufacture. A further object is the production of lactones from the corresponding saturated or unsaturated carboxylic acids or derivatives thereof.

SUMMARY OF THE INVENTION

These and other objects are achieved by the present invention which is directed to a microbiological process for the production of a gamma or delta lactone. According to this process, a culture of the fungus of the genus Mucor or an enzyme extract thereof is incubated with a substrate, which is an organic carboxylic acid having at least four carbon atoms, or a derivative thereof including a salt, an alkyl ester, a mono, di or triglyceride or an unsubstituted, monoalkyl or dialkyl amide, to produce fermentatively the gamma or delta lactone.

The organic carboxylic acid or its derivative, used as the substrate for the microbiological process of this invention may be substituted by any group that does not interfere with formation of an hydroxyl group gamma or delta to the carbonyl group of the substrate nor with the formation of the gamma or delta lactone ring. The gamma or delta lactone produced will have the same substitution pattern.

It is preferred to use as a substrate a saturated or unsaturated carboxylic acid of from four to twenty carbons in length or the corresponding derivative. The corresponding lactone produced will be a $C_4$ to $C_{20}$ gamma or delta lactone.

It is more preferred to use a substrate of the formula $R^2COZ$ wherein $R^2$ is an alkyl or alkenyl group of 3 to 19 carbons in length; Z is -OX, -OCH$_2$CHOR$^3$CHOR$^4$ or —NR$^5$R$^6$; X is hydrogen, alkyl of 1 to 6 carbons, an alkali or alkaline earth metal cation or an ion exchange resin; $R^3$ and $R^4$ independently are hydrogen, alkyl of 1 to 6 carbons or $R^2CO$; and $R^5$ and $R^6$ independently are hydrogen or alkyl of 1 to 6 carbons. The alkyl or alkenyl group may be branched or linear. It is also preferred that the four carbon moiety of the alkyl or alkenyl group which is adjacent to the COZ group is unbranched. The corresponding lactone produced has the formula

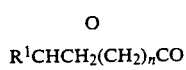

wherein n is 1 or 2 and R1 is hydrogen or alkyl of from one to sixteen carbons in length.

The nutrient broth used according to the process of the invention includes the usual sources of nitrogen, carbohydrates, minerals and oxygen. Incubative fermentation conditions used according to the process include any pH, temperature, substrate concentration and substrate feed rate which will maintain the viability of the culture.

The inventive process may be conducted in a batch or continuous mode of operation. In a batch fermentation, the nutrient broth, culture and substrate are combined and fermented until the lactone concentration becomes constant. In a continuous process, the substrate in nutrient broth may be continuously recirculated through a fermentation reactor with the provision that substrate and product are respectively added and removed from the recirculating broth.

DETAILED DESCRIPTION OF THE INVENTION

The microbiological process of the invention is useful for the production in a high yield of an optically active gamma or delta lactone from an organic carboxylic acid of at least four carbons or a derivative thereof.

Typically, the organic carboxylic acid will be a $C_4$ to $C_{20}$ alkanoic or alkenoic acid or its derivative and the corresponding lactones produced will have the formula

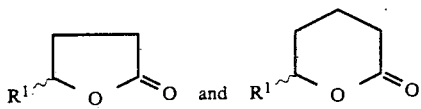

wherein the wavy lines signify the (R) and (S) enantiomers of the corresponding lactones.

The microbial transformations described herein give rise to gamma and delta lactones isomers having a high optical purity.

Such lactones are flavor and fragrance compounds. By including effective amounts of one or more of the lactones produced according to this invention, it is possible to augment or enhance the organoleptic properties of consumables such as beverages, chewing gums, fruit juices, tobacco products, pharmaceutical preparations, perfumes, perfumed products and the like. These lactones are especially valuable in certain flavor compositions where wholly natural ingredients are required.

According to the invention, conditions have now been discovered under which gamma or delta lactones of varying molecular weight can be prepared. These conditions are based upon the fermentative incubation of a fungus of the genus, *Mucor* in conjunction with the appropriate substrate in order to obtain a high yield of the desired lactone. Accordingly, it has been discovered that the transformation can be carried out in the presence of the *Mucor* fungus which can hydroxylate the carbon positioned gamma or delta to the carbonyl of the substrate. Favorable results have been obtained with members of the dimorphic fungus genera *Mucor* and preferably utilizing strains of the following species: *M. subtillissimus, M. mucedo, M. miehei, M. circinelloides, M. luteus, M. flavus, M. corticolus* and *M. albo-ater*. The substrate acid may be added directly or used in the form of its sodium salt, potassium salt, calcium salt, magnesium salt, ammonium salt, and the like. Alternatively, in place of the carboxylic acid, any of the known carboxylic acid derivatives (e.g., ester, amide, anhydride, and the like) may be employed. In the case of substrate acid esters, the alcohol portion is preferably one having 1 to 6 carbon atoms. Examples of the preferred alcohols include primary alcohols such as methanol, ethanol, n-propanol, and n-butanol, 2-methyl butanol, 3-methyl butanol and secondary alcohols such as isopropanol. Glycerol esters of the substrate acids can also be employed.

In one embodiment of the invention, the substrate utilized may be defined by the formula:

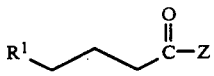

wherein $R^1$ may be hydrogen or an alkyl group containing from 1 to 17 carbon atoms; and wherein Z is defined as given above.

In carrying out the present invention, cultivation and fermentative incubation of the fungus are accomplished in an aqueous medium in the presence of the usual nutrient substances. A suitable medium is one which contains carbon sources, nitrogen sources, inorganic salts and growth factors. Among the suitable carbon sources are, for example, glucose, fructose, xylose, sucrose, maltose, lactose, mannitol, sorbitol, glycerol, corn syrup and corn syrup solids. Examples of suitable nitrogen sources include organic and inorganic nitrogen-containing substances such as peptone, corn steep liquor, meat extract, yeast extract, casein, urea, amino acids, ammonium salts, nitrates and mixtures thereof. Examples of inorganic salts include phosphates, sulfates, magnesium, sodium, calcium, and potassium. These nutrients may be supplemented with, for example, one or more vitamins of the B group and one or more trace minerals such as iron, manganese, cobalt, copper as desired. For the nutrient broth, it is preferred to utilize dextrose at a concentration of about 2 to about 20 weight percent, more preferably about 4 to about 15 weight percent, and most preferably about 8 to 12 weight percent. It is also preferred to employ B vitamins either as a separate supplement or in the form of a yeast extract. The kind and amounts of the above mentioned additives can be determined by applying the general knowledge in the art for the cultivation of microorganisms.

In a typical procedure, the Mucor fungus is first cultivated in inoculum quantities to produce a mature culture in nutrient broth. The culture is inoculated into a fermentor nutrient broth and allowed to establish itself. The substrate is then added and fermentation continued until a steady concentration of lactone is present.

The cultivation and fermentative incubation of the fungus can be carried out as a stationary culture or as a submerged culture (e.g., shake-flask, fermentor), preferably under aerobic conditions. Cultivation and incubation suitably may proceed in a pH range of from about 3 to about 9, preferably in the range of from about 4 to about 8, and most preferably about 6 to about 7. The pH may be regulated by the addition of an inorganic or organic acid or base such as hydrochloric acid, acetic acid, sodium hydroxide, calcium carbonate, ammonia, ion-exchange resins, or by the addition of a buffer such as phosphate, phthalate or Tris ®. The incubation temperature is suitably maintained at between about 18° C. and about 31° C., with a range from about 20° C. to about 28° C. being preferred and a range from about 24° C. to about 27° C. being especially preferred.

In accordance with another typical procedure of the present invention, the process is conveniently carried out by adding the substrate to the culture medium at the onset of cultivation, under aerobic conditions. Alternatively, the substrate may be added either alone or in combination with another carbon source, such as glucose, during fermentative incubation, or when cultivation is complete. It is preferable to add the substrate to the culture medium during the period of from 7 up to 24 hours after the growth of the culture in the fermentative broth has commenced. Desirable results can be obtained when the substrate is added continuously over the entire fermentation after an initial fungal cultivation period of from 7 up to 12 hours. A preferred feed rate for this continuous addition is 0.001 to 2 g per hour per liter of broth, more preferred 0.01 to 1 g per hour per liter, and most preferred 0.6 to 0.8 g per hour per liter. The concentration of the substrate in the medium may vary depending on the conditions employed. In practice, the concentration of the substrate in the medium may conveniently vary from 0.01% to about 10%, preferably about 0.1% to about 5%, more preferably 0.5 to about 2% by weight consistent with the manner in which it is added to the culture.

Under the usual conditions, mixtures of optically active gamma and delta lactones are generally produced with the gamma lactone being substantially favored. While adjustment of pH, oxygen, nutrients, and the Z group of the substrate can cause variation of the relative ratio of gamma to delta lactone, the ratio often will favor the gamma lactone. However, under certain conditions and with certain Mucor species, the delta lactone is favored. The examples teach the details for variation of the ratio of gamma to delta lactone. The lactone mixtures can be utilized as is or further purified to recver the pure gamma and/or delta lactones.

The reaction period varies according to the specific incubation parameters, such as the strain of microorganism employed, the composition of the culture medium and the substrate present. In general, shake flask cultures require from between 2 hours and about 240 hours, preferably 48 to 192 hours, more preferably 72 to 144 hours, depending upon the microbial strain and the substrate utilized. However, when a fermentor is used, the fermentation period may be reduced to 90 hours or less.

The incubation is carried out under aerobic conditions, wherein the dissolved oxygen content in the incubation broth is from 20 to 100% by weight, preferably 30% to 80%, more preferably 40 to 60%. Also, preferably, the substrate is maintained in continuous contact with the aqueous phase and the microorganism. Generally, vigorous stirring or shaking is satisfactory, but if desired a surface active agent, such as Tween 80, can be added to aid in the dispersion of the substrate. Conventional antifoam agents such as silicone oils, polyalkylene glycol derivatives, or soya oil can be used to control foaming.

The form in which the microorganisms are used for the fermentation is not critical. The fermentation may be carried out using the cells of the microorganism isolated from the culture solution, or with an enzyme extract isolated from the cells in a known manner. In the latter case, reaction can be conveniently carried out in an aqueous solution, for example in a buffer solution, in a physiological saline solution, in a fresh nutrient solution, or in water. The isolated cells or an enzyme extract thereof may be immobilized on a solid support and the desired transformation conducted separately. It will be convenient to employ the immobilized form of the enzyme extract in a continuous process. The fermentation of the substrate may also be effected by mutants of the fungus.

The progress of the fermentative production of the lactone can be monitored by assaying for lactone concentration using standard analytical techniques such as chromatography (gas-liquid, thin layer or high pressure liquid) and spectroscopy such as IR and NMR. The fermentation can also be followed by measuring consumption of substrate, glucose, oxygen or by measuring pH changes. The fermentation is generally terminated when all of the substrate has been consumed or when no further increase in the lactone concentration is observed.

Isolation and purification of the final products of the present invention can be achieved by conventional techniques which include solvent extraction, distillation, chromatographic separation, high pressure liquid chromatography and the like.

The present invention avoids the complicated steps required to produce lactones by conventional synthetic methods and produces a high yield of lactone (e.g. 5-15 grams per liter of broth) compared with conventional fermentation methods which yield products at best on the order of several milligrams per liter.

The following examples are set forth to more fully illustrate embodiments of the invention but are in no way meant to limit the scope thereof.

EXAMPLE 1

*M. subtillissimus fermentation*

A culture of ten ml of a 24 h broth culture of *Mucor subtillissimus* (FDO isolate 5.6) was inoculated in 200 ml of sterile broth containing 2g peptone, 1 g yeast extract and 20 g dextrose, (hereinafter referred to as PYE broth). The culture was incubated at 27° C. and agitated at 250 rpm for 21 hr. At this time the pH of the culture was adjusted to 7.0 and 1.5 g of ethyl hexanoate was added. After an additional 48 h fermentation period, during which the pH was adjusted to 7.0 every 24 h, the culture broth was extracted with methylene chloride and the extract was analyzed by gas chromatography. After distillation the recovered extract weighed 0.75 g and contained 5.2% of delta-hexalactone and 0.9% of gamma-hexalactone. Further results using different growth media and substrates are shown in Table I. In all cases the extract accounted for 40 to 50%, by weight, of the added substrate.

TABLE I

| Medium | Substrate (Concentration) | Incubation Period (days) | Lactones Isolated | Yield (% Composition in Extract) |
| --- | --- | --- | --- | --- |
| YM broth[1] | methyl hexanoate (1%) | 2-3 | delta-hexalactone gamma-hexalactone | 7.7 1.9 |
| YM broth | methyl octanoate (1%) | 2.3 | gamma-octalactone delta-octalactone | trace (i.e. <0.1%) trace |
| YM broth | hexanoic acid (0.5%) | 6 | gamma-hexalactone | 0.5 |
| YM broth | octanoic acid (0.5%) | 6 | gamma-octalactone | 2.4% |
| PYE broth[2] | methyl hexanoate (1.5%) | 4 | delta-hexalactone gamma-hexalactone | 1.1% trace |

TABLE I-continued

| Medium | Substrate (Concentration) | Incubation Period (days) | Lactones Isolated | Yield (% Composition in Extract) |
|---|---|---|---|---|
| PYE broth | ethyl hexanoate (1.5%) | 4 | delta-hexalactone | 5.2% |
|  |  |  | gamma-hexalactone | 0.9 |
| PYE broth | 2-methyl butyl hexanoate (1.5%) | 4 | gamma-hexalactone | 0.4 |
|  |  |  | delta-hexalactone | trace |
|  |  |  | gamma-octalactone | 0.5 |
|  |  |  | delta-octalactone | 1.5 |
| PYE broth | methyl octanoate ethyl octanoate or 2-methyl butyl octanoate (1.5%) | 4 | gamma-octalactone | trace |
|  |  |  | delta-octalactone | trace |
| PYE broth | methyl decanoate (1.5%) | 3 | gamma-decalactone | trace |
| PYE broth | ethyl decanoate (1.5%) | 3 | gamma-decalactone | trace |
| PYE broth | ethyl-4-methyl nonanoate (1%) |  | delta-nonalactone | trace |

[1]Difco Laboratories.
[2]PYE broth is composed of 1% peptone 0.5% yeast extract, 10% dextrose.

EXAMPLE 2

*M. circinelloides fermentation*

Ten ml of a 24 h broth culture of Mucor circinelloides (FDO isolate 9.17) was inoculated in 200 ml PYE broth. After 24 h of incubation under the above conditions the pH was adjusted to 7.0 and 1.5 g of ethyl octanoate was added. After an additional 48 h fermentation the broth was extracted with organic solvent. The recovered extract weighed 0.8 g and contained 49.4% gamma-octalactone and a trace of delta-octalactone. Further results using different growth media and substrates are shown in Table II.

Although the FDO strain of Mucor circinelloides is morphologically similar to strains presently on deposit at the major culture collections, it appears to produce lactones in higher yields. Therefore the FDO culture has been submitted to ATCC to be categorized.

EXAMPLE 3

Fermentation Using Several Mucor Species and An Ester

Each of the following *Mucor* species was cultured in PYE broth as previously described for 24 to 48 hours prior to the addition of 1% (v/v) of ethyl octanoate. The cultures were extracted after an additional 3 to 5 days of fermentation and the extracts were subjected to analysis by gas chromatography. Each extract accounted for 40 to 60%, by weight, of the added substrate, except where otherwise noted. Results are shown in Table III below.

TABLE III

| ORGANISM | STRAIN No.[a] | Yield of Gamma-Octalactone (% Composition of Extract) |
|---|---|---|
| M. circinelloides | 8540 | 15.8 |
| M. circinelloides | 8542 | 3.2 |
| M. circinelloides | 1207a | 8.9 |
| M. circinelloides | 27649* | 10.7 |
| M. circinelloides | 27749* | 8.0 |

TABLE II

| Medium | Substrate (Concentration) | Incubation Period (days) | Lactones Isolated | Yield (% Composition in Extract) | [alpha]$_D$ |
|---|---|---|---|---|---|
| PYE broth (1%) | methyl hexanoate | 4 | delta-hexalactone | 1.4 | +31.6 |
| PYE broth (1.5%) | ethyl hexanoate | 4 | gamma-hexalactone | 1.7 | +39.8 |
|  |  |  | delta-hexalactone | 2.9 | +31.6 |
| PYE broth | 2-methyl butyl hexanoate (1.5%) | 3 | gamma-hexalactone | 10.8 | NM |
|  |  |  | delta-hexalactone | trace | NM |
| PYE broth | methyl octanoate (1.5%) | 3 | gamma-octalactone | 6.2 | NM |
|  |  |  | delta-octalactone | trace | NM |
| PYE broth | ethyl hexanoate (1.5%) | 3 | gamma-octalactone | 49.4 | −39.8 |
|  |  |  | delta-octalactone | trace | NM |
| PYE broth | 2-methyl butyl octanoate (1.5%) | 3 | gamma-octalactone | 3.0 | −40.0 |
| PYE broth | coconut oil (2%) (1.5%) | 4 | gamma-octalactone | trace | NM |
| PYE broth | octanoic acid[3] (1.5%) | 4 | delta-octalactone | 25.0 | NM |
| PYE broth | ethyl decanoate (1.5%) | 3 | gamma-hexalactone | 1.2 | NM |
|  |  |  | gamma-octalactone | 3.0 | NM |
|  |  |  | delta-decalactone | 2.0 | NM |
| PYE broth | methyl decanoate | 3 | gamma-octalactone | 3.0 | NM |
|  |  |  | gamma-decalactone | 14.0 | −27.1 |
| PYE broth | octanamide (0.5%) | 3 | gamma-octalactone | 9.0 | NM |
|  |  |  | delta-octalactone | 1.7 | NM |

[3]This culture contained 20 g of Dowex 203, an anion resin used to bind the free acid in order to limit the side effects thereof.
NM = not measured.

TABLE III-continued

| ORGANISM | STRAIN No.[a] | Yield of Gamma-Octalactone (% Composition of Extract) |
|---|---|---|
| M. circinelloides | 42258 | 29.4 |
| M. hiemalis | 24435* | 20.9 |
| M. hiemalis | 28840 | 2.9 |
| M. hiemalis | 20028* | 8.0 |
| M. hiemalis | 28841 | 92.1[b] |
| M. hiemalis | 24335* | 84.1[b] |
| M. albo-ater | 42256 | 35.4 |
| M. circinelloides | 1207b | 20.6 |
| M. circinelloides | 42257 | 97.3[b] |
| M. corticolus | 18358 | 62.6[b] |
| M. corticolus | 18359 | 53.3[b] |
| M. albo-ater | 42255 | 22.0 |
| M. mucedo | 62756** | trace |
| M. leutus | 28932 | 37.4 |
| M. sps | 5607 | 75.8[b] |

[a]Strain number refers to ATCC except where noted.
* = CBS; = NRRL; ** = DSM.
[b]After 5 days of fermentation with substrate the percent recovery (by weight) in these samples was 10% or less.

EXAMPLE 4

Fermentation Using Several Mucor Species and An Amide

Each of the following *Mucor* species was cultured in PYE broth as previously described for 24 hours, prior to the addition of 0.5% (w/v) octanamide and 1.5% (v/v) Tween 80. The cultures were extracted after an additional 3 days fermentation and the extracts were subjected to analysis by gas chromatography. Each extract accounted for 50–60%, by weight, of the added substrate. Results are shown in Table IV below.

TABLE IV

| ORGANISM | STRAIN No. | Yield of Octalactones (% Composition of Extract) | |
|---|---|---|---|
| M. corticolus | 18358 | gamma = 25.0 | delta = 0.4 |
| Mucor sps | 5607 | gamma = 3.3 | delta = 0.0 |
| M. circinelloides | 24435 | gamma = 2.8 | delta = 2.0 |
| M. hiemalis | 8542 | gamma = 5.0 | delta = 0.3 |
| M. hiemalis | 20028 | gamma = 5.0 | delta = 0.0 |
| M. circinelloides | 1207b | gamma = 2.5 | delta = 1.5 |

EXAMPLE 5

Large Scale Fermentation of M. circinelloides and Ester

A 5L fermentation vessel containing 4L of PYE broth was inoculated with 800 ml of 20 h culture of *M. circinelloides*. (FDO isolate 9.17) Temperature was maintained at 27° C., pH was maintained at 7.1 (+0.2), oxygen concentration was maintained at 50% saturation (±15%) via automatic controls. After 7 h of incubation ethyl octanoate was pumped into the broth at a rate of 0.7 ml/L broth/h for a total fermentation time of 40 h. One liter of this broth was acidified and extracted with methylene chloride. The extract weighed 25 g and 20 g was recovered after distillation. The distillate contained 56% gamma-octalactone which equals 11.2 g lactone recovered per liter of fermentation broth.

EXAMPLE 6

Large Scale Fermentation of M. subtillissimus and Ester

Fifteen liters of PYE broth was inoculated with 400 ml of a 20 h PYE broth culture of *Mucor subtillissimus* (FDO Isolate 5.6) in a 20 L fermentor. The temperature was maintained at 27° C., pH at 6.5, dissolved oxygen concentration at 50% saturation, via automatic controls. After 5 h of incubation in the fermentor vessel, ethyl caproate was pumped into the culture at a rate of 0.4 ml/h/liter culture broth, for the next 24 h. The broth was then acidified and extracted with an organic solvent. After distillation, 25 g of sample was recovered and this sample contained 2.6 g gamma-hexalactone, 7.3 g delta-hexalactone and 13.5 caproic acid.

EXAMPLE 7

Large Scale Fermentation of M. hiemalis and an Ester

Fifteen liters of PYE broth was inoculated with 100 ml of a 24 h PYE broth culture of *Mucor hiemalis* ATCC No. 20028 in a 20L fermentor. The temperature was maintained at 27° C., pH at 6.5 and dissolved oxygen at 20%. After 18 h of incubation in the fermentor vessel, ethyl decanoate was pumped into the culture at a rate of 0.6 ml/h/liter broth, for the next 52 h. The culture was then acidified and extracted with an organic solvent. A total of 133 g was recovered after the extract was distilled and this sample contained 3 g of gamma-decalactone with the remainder being a mixture of hydroxy esters and acids.

EXAMPLE 8

Apricot Flavored Drink

An aqueous sugar stock can be prepared by dissolving 20 g sucrose and 0.1 g salt in 1L water. To 2L of this aqueous stock can then be added about 0.2 g of a mixture of the following lactones gamma hexalactone (10%), gamma and delta octalactones (40%) gamma and delta decalactones (40%) and gamma dodecalactone (10%) the percentages being by weight of the total mixture. About 1 to 2 g of gum alginate can be added to the mixture to provide body and 0.5 to 1 g lecithin as an emulsifier.

The mixture can be placed in a high speed blender to homogenize it and then may be bottled and refrigerated. The resulting product is a sweet beverage having an apricot-like taste.

What is claimed is:

1. A microbiological process for the production of $C_4$ to $C_{20}$ delta or gamma lactones which comprises:
    incubating in nutrient broth a culture of a fungus of the genus *Mucor* with a substrate comprising a saturated or unsaturated carboxylic acid of from four to twenty carbon atoms in length, a salt thereof, an alkyl ester thereof, a mono, di or triglyceride thereof or an unsubstituted monoalkyl or dialkyl amide thereof, thereby producing the lactone in a recoverable amount.

2. A process according to claim 1 wherein the lactone has the formula

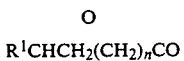

$$R^1CHCH_2(CH_2)_nCO$$

wherein n is 1 or 2 and $R^1$ is hydrogen or alkyl of from one for fifteen carbons in length.

3. A process according to claim 2 wherein the substrate has the formula:

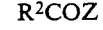

$$R^2COZ$$

wherein $R^2$ is an alkyl or alkenyl group of 3 to 19 carbons in length; Z is $-OX$, $-OCH_2CHOR^3CHOR^4$ or $-NR^5R^6$; X is hydrogen, alkyl of 1 to 6 carbons, an alkali or alkaline earth metal cation or an ion exchange resin; $R^3$ and $R^4$ independently are hydrogen, alkyl of 1 to 6 carbons or $R^2CO$; and $R^5$ $R^6$ independently are hydrogen or alkyl of 1 to 6 carbons.

4. A process according to claim 3 wherein at least the four carbon moiety of the alkyl or alkenyl group which is adjacent to the COZ group is unbranched.

5. A process according to claim 1 wherein the incubation is conducted at a pH of about 3 to about 9, a temperature of about 18° C. to 31° C., and the nutrient broth has nutrient sources of nitrogen and carbohydrate and is in contact with an atmosphere containing from about 18% to about 100% oxygen.

6. A process according to claim 1 wherein the substrate concentration in the nutrient broth is from about 0.01% to about 10% by weight, relative to the total weight of the nutrient broth, the substrate is continuously added at a feed rate of from about 1 mg to about 2 g per hour per liter of nutrient broth, and the incubation period is about 1 to 10 days.

7. A process according to claim 5 wherein the substrate concentration in the nutrient broth is from about 0.01% to about 10% by weight relative to the total weight of the nutrient broth, the nitrogen source is a peptone at a concentration of about 0.01 to about 3% by weight relative to the total weight of the broth and a yeast extract at a concentration of about 0.1 to 2% by weight, the carbohydrate is dextrose at a concentration of about 2% to about 20% by weight relative to the weight of the broth, the substrate is continuously added at a feed rate of from about 1 mg to about 2 g per hour per liter of nutrient broth, and the incubation period is about 1 to 10 days.

8. A process according to claim 7 wherein the pH is about 4 to 8, the temperature is about 20° C. to about 28° C., the yeast extract concentration is from about 0.1 to about 2%, the peptone concentration is from about 0.1 to 2%, the dextrose concentration is from about 4% to about 15%, the atmosphere contains from about 30% to about 80% oxygen, the substrate concentration is from about 0.1% to about 5%, the feed rate is from about 0.01 g to 1 g per hour per liter and the incubation period is from about 2 to 8 days.

9. A process according to claim 7 wherein the pH is about 6 to about 7, the temperature is about 24° C. to about 27° C., the yeast extract concentration is about 0.5% to about 1%, the peptone concentration is from 0.1 to 2%, the dextrose concentration is about 8% to about 12%, the atmosphere contains from about 40% to about 60% oxygen, the substrate concentration is from 0.5% to about 2%, the feed rate is from about 0.6 to about 0.8 g per hour per liter and the incubation period is from about 3 to 6 days.

10. A process according to claim 7 wherein the pH is about 6 to about 7, the dextrose concentration at the beginning of the incubation is about 10%, B vitamins are added as a supplement, the substrate feed rate is about 0.6 g per hour per liter and the atmosphere is about 40% to 60% oxygen.

11. A process of claim 10 wherein the B vitamins are added in the form of a yeast extract.

12. A process according to claim 1 further comprising monitoring the lactone concentration in the nutrient broth and terminating the incubation when the concentration of lactone remains about constant.

13. A process according to claim 1 wherein the substrate is the alkyl ester.

14. A process according to claim 13 wherein the alkyl group is 1 to 3 carbons in length.

15. A process according to claim 1 wherein the substrate is the unsubstituted amide.

16. A process according to claim 1 wherein a mixture of the gamma and delta lactones is produced.

17. A process according to claim 16 wherein the mixture substantially comprises the delta lactone.

18. A process according to claim 16 wherein the mixture substantially comprises the gamma lactone.

19. A process according to claim 16 wherein the gamma and delta lactones are separated.

20. A process according to claim 1 wherein the gamma or delta lactone is optically active.

21. A process according to claim 1 wherein the gamma or delta lactone is a mixture of optical isomers.

22. A process according to claim 1 wherein the gamma lactone is produced.

23. A process according to claim 1 wherein the delta lactone is produced.

24. A process according to claim 1 wherein gamma-octalactone is produced.

25. A process according to claim 1 wherein the substrate is ethyl octanoate.

26. A process according to claim 1 wherein the living fungus is used as the culture.

27. A microbiological process for the production of a $C_{21}$ gamma or delta lactone comprising:
incubation in a nutrient broth a culture of a *Mucor* fungus with a substrate comprising a saturated or unsaturated carboxylic acid containing twenty-one carbon atoms, a salt, alkyl ester, mono-, di- or triglyceride thereof, or an unsubstituted monoalkyl or dialkyl amide thereof, thereby producing the lactone in a recoverable amount.

* * * * *